(12) United States Patent
Deck

(10) Patent No.: US 8,828,037 B2
(45) Date of Patent: Sep. 9, 2014

(54) ELECTROMECHANICAL PRICKING AID FOR TAKING LIQUID SAMPLES

(75) Inventor: Frank Deck, Niederkirchen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1345 days.

(21) Appl. No.: 11/833,042

(22) Filed: Aug. 2, 2007

(65) Prior Publication Data

US 2008/0015623 A1    Jan. 17, 2008

Related U.S. Application Data

(63) Continuation of application No. PCT/EP2006/050530, filed on Jan. 30, 2006.

(30) Foreign Application Priority Data

Feb. 3, 2005 (DE) .......................... 10 2005 005 017

(51) Int. Cl.
*A61B 17/32* (2006.01)
(52) U.S. Cl.
USPC ......................................................... 606/181
(58) Field of Classification Search
CPC ............. A61B 5/1411; A61B 5/15146; A61B 2560/0456
USPC ................. 606/181, 182, 183, 184, 185, 186; 600/583, 573
See application file for complete search history.

(56) References Cited

U.S. PATENT DOCUMENTS

| | | | | |
|---|---|---|---|---|
| 5,047,044 A | * | 9/1991 | Smith et al. | 606/182 |
| 5,474,566 A | * | 12/1995 | Alesi et al. | 606/139 |
| 5,690,618 A | * | 11/1997 | Smith et al. | 604/232 |
| 5,836,894 A | * | 11/1998 | Sarvazyan | 600/587 |
| 6,210,420 B1 | | 4/2001 | Mauze et al. | |
| 6,524,240 B1 | * | 2/2003 | Thede | 600/300 |
| 6,530,892 B1 | | 3/2003 | Kelly | |
| 6,616,616 B2 | | 9/2003 | Fritz et al. | |
| 8,075,496 B2 | * | 12/2011 | Deck et al. | 600/583 |
| 2001/0053888 A1 | * | 12/2001 | Athanasiou et al. | 604/154 |
| 2002/0103499 A1 | * | 8/2002 | Perez et al. | 606/182 |
| 2002/0130042 A1 | * | 9/2002 | Moerman et al. | 204/403.01 |
| 2002/0170823 A1 | | 11/2002 | Housefield et al. | |
| 2003/0083686 A1 | * | 5/2003 | Freeman et al. | 606/181 |

(Continued)

FOREIGN PATENT DOCUMENTS

| | | |
|---|---|---|
| DE | 40 36 479 | 5/1992 |
| DE | 10047419 | 4/2002 |

(Continued)

*Primary Examiner* — Tuan V Nguyen
*Assistant Examiner* — Tin Nguyen
(74) *Attorney, Agent, or Firm* — Roche Diagnostics Operations, Inc.

(57) ABSTRACT

A portable lancing aid for providing liquid samples comprises a lancet system having at least one lancet, a tensioning device, and an electromechanical actuator. The tensioning device can be tensioned by the electromechanical actuator. The portable lancing aid may further include an energy source for storing electrical energy that is connected to the electromechanical actuator. Additionally, the portable lancing aid may include an interface for charging the energy source where the interface is externally accessible from the lancet system. The invention is ergonomical and easy to handle for children and patients with physical limitations. Furthermore, a lancing system for collecting liquid samples is provided with a portable lancing aid that is detachably mountable to a charging station for charging the portable lancing aid.

20 Claims, 3 Drawing Sheets

(56) References Cited

U.S. PATENT DOCUMENTS

| | | |
|---|---|---|
| 2004/0010279 A1* | 1/2004 | Freeman et al. .............. 606/182 |
| 2004/0092996 A1 | 5/2004 | List et al. |
| 2004/0098009 A1 | 5/2004 | Boecker |
| 2004/0215224 A1* | 10/2004 | Sakata et al. .................. 606/181 |
| 2004/0260325 A1 | 12/2004 | Kuhr et al. |
| 2006/0008389 A1 | 1/2006 | Sacherer et al. |
| 2007/0213638 A1* | 9/2007 | Herbrechtsmeier et al. .. 600/583 |

FOREIGN PATENT DOCUMENTS

| | | |
|---|---|---|
| DE | 102 23 558 | 12/2003 |
| DE | 103 12 357 | 7/2004 |
| DE | 10302501 | 8/2004 |
| EP | 0 449 525 | 12/1991 |
| WO | WO 03/086103 | 10/2003 |
| WO | WO 2004/060143 | 7/2004 |
| WO | WO 2005/001418 | 1/2005 |

* cited by examiner

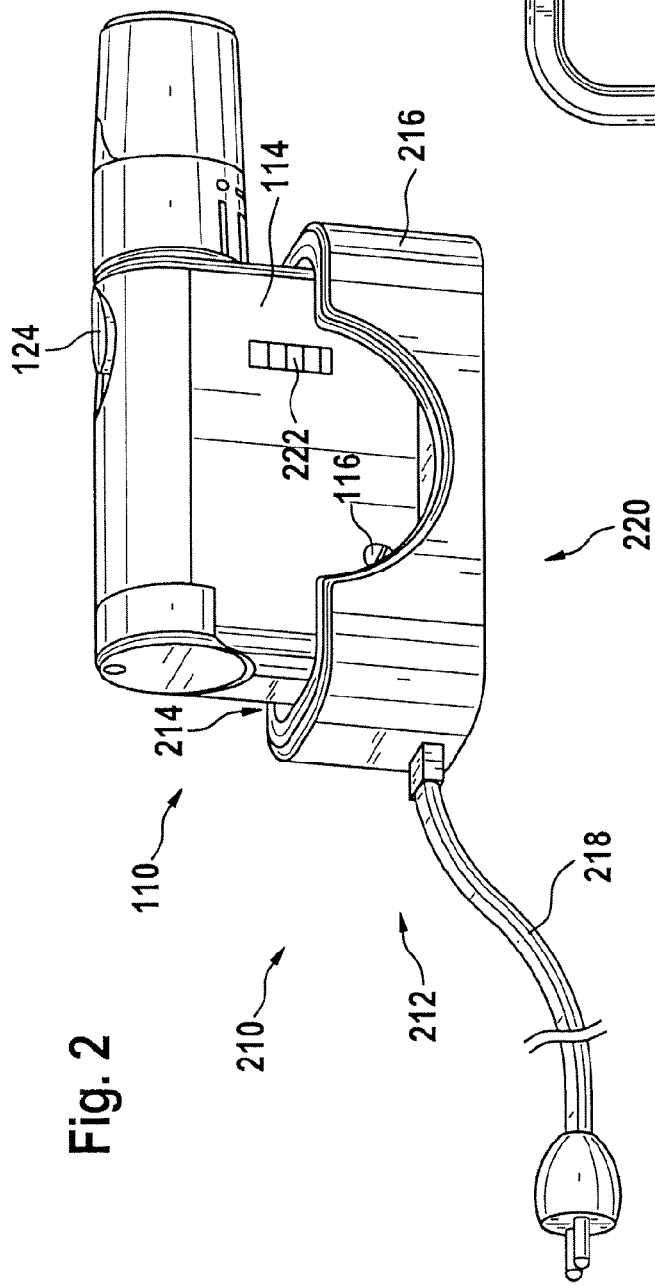
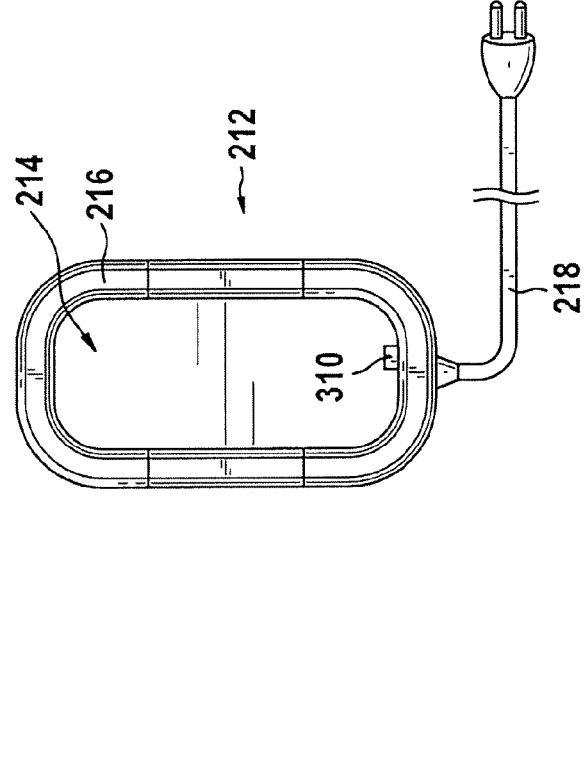

US 8,828,037 B2

ELECTROMECHANICAL PRICKING AID FOR TAKING LIQUID SAMPLES

RELATED APPLICATIONS

This is a continuation application of International Application PCT/EP2006/050530, filed Jan. 30, 2006, which claims priority to DE 10 2005 005 017.4, filed Feb. 3, 2005, which are hereby incorporated by reference in their entirety.

BACKGROUND

Monitoring blood glucose concentration is an essential part of the daily routine for diabetics. Blood glucose concentration must be determined rapidly and with ease several times daily in order to take appropriate medical measurements. In order to not restrict the daily routine of the diabetic more than necessary, mobile devices which are space-saving and simple to handle are used so that blood glucose concentration can be determined at any time.

Measurement of blood glucose concentration essentially requires two procedural steps. First, a liquid sample is generally produced by perforating the skin of the patient by means of a so-called lancet system, e.g., with the aid of a lancet needle driven by a spring system to generate a drop of blood. A blood quantity of 1.5 µL (or sometimes below 1 µL) is generally sufficient for modern measurement systems. Such lancet systems and lancing aids are known in the art and are commercially available in various embodiments. Such lancet systems are described, for example, in Publication Nos. DE 10 302 501 and DE 10 047 419. Lancing aids with magazine systems for holding and dispensing several lancets are also disclosed in these documents.

Second, the blood sample generated is then analyzed for blood glucose concentration. Diagnostic methods are usually used for this step and employ optical or electrochemical measuring methods. For example, a frequently used measuring method utilizes a special type of electrochemical test strip which can be designed such that a specified amount of blood is guided by a capillary system to an electrode system. This electrode system can, for example, be gold electrodes which are provided with a coating. The coating usually contains various enzymes and mediators and has the effect that charge carriers (for example, in the form of redox molecules) form within the blood sample at the electrodes. The concentration of the charge carriers are dependent on blood glucose concentration and can be determined by the gold electrodes and a suitable measuring system known to a person skilled in the art, for example, by means of a comparatively simple current-voltage measurement from which blood glucose concentration can be calculated.

Such a test device is known from U.S. Publication No. 20020170823, which can be used for substance analysis in body fluids such as for measuring blood glucose concentration. The described measuring device has a hand-held device and a base station in which the hand-held device and the base station can exchange data via an interface. The portable hand-held device is powered by lithium batteries.

In the first step described above for generating a blood sample, the lancet system usually first has to be manually tensioned when using systems and lancing aids known in the prior art. A spring system is typically manually tensioned, which requires a user to apply force in order to create the tension. However, this has disadvantages because children or people with physical limitations cannot usually use such lancing aids without help, and the use of such systems is inconvenient. Furthermore, operating some of these lancing aids with one hand is not always possible due to the required tensioning process.

SUMMARY OF THE INVENTION

Embodiments incorporating the present invention address the described disadvantages of the prior art and provide a portable lancing aid for collecting liquid samples and, in particular, for collecting blood samples for determining blood glucose concentrations. The portable lancing aid is easy to operate, especially for children or patients with physical limitations. Furthermore, additional embodiments provide a system for collecting liquid samples which has a portable lancing aid and a charging station for charging at least one long-term energy storage component of the portable lancing aid.

An exemplary embodiment of the portable lancing aid has at least one lancet system, wherein the lancet system has at least one lancet and at least one tensioning device for tensioning the lancet system. This lancet system can be one with a tensioning device that has a spring system such as those found in the prior art. This embodiment of the portable lancing aid is also flexible with regard to the design of the lancet and thus any lancet known to a person skilled in the art may be used. For example, the lancet can have at least one lancet needle, and in particular, a disposable lancet needle which for hygienic purposes is replaced by a new lancet needle after one or more lancing operations. Instead of lancet needles, the lancet can also have analogous designs such as prism-shaped, sharp-edged lancets. In particular, the portable lancing aid can have a single lancet or a plurality of lancets. In one embodiment with a plurality of lancets, a magazine for holding and/or dispensing lancets is advantageously used. An exemplary magazine is described in Publication No. DE 10 302 501.

In another embodiment, the portable lancing aid has at least one electromechanical actuator that tensions the tensioning device. The electromechanical actuator advantageously has at least one electric motor such as a direct current motor. It is further possible to use other electromechanical actuators such as magnetic systems (e.g., electromagnets) or piezoelectric systems. The electromechanical actuator can, for example, be directly connected to the lancet system, and in particular, with the tensioning device, or it can be connected by one or more gear units. The gear unit can, for example, have a drive mechanism via one or more drive belts or one or more gear wheels.

In addition, one embodiment of the portable lancing aid has at least one rechargeable long-term energy source that is connected to the electromechanical actuator in order to store electrical energy. In this embodiment, the energy source is used for storing electrical energy and remains substantially charged even after days if there is no electrical load. In particular, the electrical energy or charge should not decrease below 40% of the original energy or charge within about three days. This long-term energy source can be a battery and it has proven to be advantageous in various embodiments to use rechargeable batteries such as rechargeable lithium ion batteries and/or rechargeable lithium polymer batteries. It is also possible to use rechargeable nickel cadmium batteries and/or rechargeable nickel metal hydride batteries (NimH). However, it is also possible to use other types of rechargeable batteries. Thus, for example, capacitors having a long-term storage effect such as "supercaps" (also referred to as ultra capacitors) can also be used. Stored electrical energy can also be partially removed from these supercaps similar to batteries or rechargeable batteries and the self-discharge of these components is very low. Typical supercaps still have about 60-70% of their original charge after 30 days without load. Such components have the particular advantage over conventional rechargeable batteries in that they can be rapidly charged.

In another embodiment, the portable lancing aid has at least one interface that is accessible from outside the lancet system, wherein the long-term energy source can be connected to the interface in order to store electrical energy and be recharged. This interface can be one or more electrodes, such as metal electrodes, which are arranged on the outside of the housing. An appropriate complementary interface (e.g., a charging interface or charging station) can then be used to supply energy to these metal electrodes via connection to an appropriate power supply unit. This allows the energy source of the portable lancing aid to be recharged at regular intervals.

In another embodiment, the interface can also have a device for inductively charging the long-term energy source. For example, the interface can have a secondary coil of a transformer that is electrically connected to the energy source and a transformer core such that the energy source can be inductively charged essentially by putting a primary coil on the transformer core and applying an alternating voltage to this primary coil. This primary coil can, for example, be a component of a charging station into which the portable lancing aid is inserted.

The charging operation can take place when a charge level indicator shows that the charge level is below the minimum charge value for the long-term energy source. Hence, it has proven to be advantageous in one embodiment when the portable lancing aid has a charge level indicator to display the electrical charge level of the energy source for storing electrical energy. Such charge level indicators are known to a person skilled in the art and can, for example, have simple optical displays and/or acoustic indicators. In particular, the charge level indicator can have an optical segment display in the form of one or more light-emitting diodes which indicate the charge level of the energy source. Furthermore, the user of the portable lancing aid can also be given a warning such as an alarm such as an optical or acoustic signal when the charge level of the energy source reaches or falls below a specified minimum charge level. Thus, the user can be warned when the charge level of the energy source is no longer adequate to tension the lancet system or when the charge level is only sufficient for a few tensioning operations (for example, enough energy for a daily number of blood glucose measurements). This prevents the user or patient from not being able to carry out blood glucose measurements due to an unexpectedly uncharged energy source of the portable lancing device.

Embodiments of the portable lancing aid are advantageous over lancing aids in the prior art because the user no longer has to exert any mechanical force to tension the lancet system. The lancet system is instead tensioned by the electromechanical actuator. Hence, the portable lancing aid can also be used comfortably by patients with physical limitations or by children. The portable lancing aid can also be easily operated with one hand. If the charge level of the energy source and, in particular of the rechargeable battery, falls below a specified minimum value, the user or patient is warned accordingly so that the energy source can either be recharged or replaced. In addition, an embodiment of the device can also be provided in which the tensioning device is manually tensioned so that the lancet system can still be tensioned even when the energy source is empty or almost empty, but in this case the patient has to exert a mechanical force.

In an exemplary embodiment, the portable lancing aid can include at least one tensioning status sensor which detects the tensioning state of the tensioning device. Furthermore, means can be provided such as an appropriate electronic device or element (e.g., a microcomputer or other electronic components) to analyze the detected state of tension of the tensioning device. A tensioning operation can then be triggered depending on the detected state of tension. If it is, for example, found that the lancet system is in an untensioned state (e.g., after the lancet system has been triggered), the tensioning device can be automatically retensioned. The portable lancing aid is thus again ready for operation and further intervention by the user is not necessary. This embodiment is especially advantageous in combination with a portable lancing aid having a magazine for holding a plurality of lancets. In this embodiment, the system is designed such that a new lancet is selected automatically for each tensioning operation and prevents unhygienic multiple use of the same lancet. In an alternative embodiment, the lancet can be selected manually by the user, for example, by means of an appropriate rotary knob connected to the magazine.

In an advantageous embodiment, the system for collecting liquid samples includes a charging station to charge the long-term energy source of the portable lancing aid. In this embodiment, one or more portable lancing aids can be connected to a charging station. Such charging stations are known from various fields of the state of the art. In addition to the base station disclosed in U.S. Publication No. 20020170823, such systems are also disclosed in U.S. Pat. No. 6,524,240 for charging portable medical devices. An example of an electronic circuit of a charging station which prevents a portable instrument that is inserted into the charging station from being actuated when a charging current flows is disclosed in Publication No. DE 4036479.

The charging station can, for example, have at least one charging interface or coupling which can be connected to a source of electrical energy. This connection can be via one or more switches (for example selection switches or on/off switches) or via an electronic circuit so that an appropriate voltage transformation, an overvoltage protection, and/or an appropriate interval timer can be used which simplifies the handling of the system and makes a safer design. In this embodiment, it should be possible to connect the portable lancing aid to the charging station such that the charging interface or coupling is connected to the interface of the portable lancing aid. This connection between the portable lancing aid and the charging station can be accomplished by inserting the portable lancing aid into a corresponding recess of the charging station where the portable lancing aid is advantageously aligned during insertion such that the interface of the portable lancing aid is in electrical contact with the interface or coupling of the charging station.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein:

FIG. 2 is a perspective view of a system for collecting liquid samples showing the portable lancing aid of FIG. 1 and a charging station;

FIG. 3 is a top view of the charging station of FIG. 2; and

Corresponding reference numerals are used to indicate corresponding parts throughout the several views.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
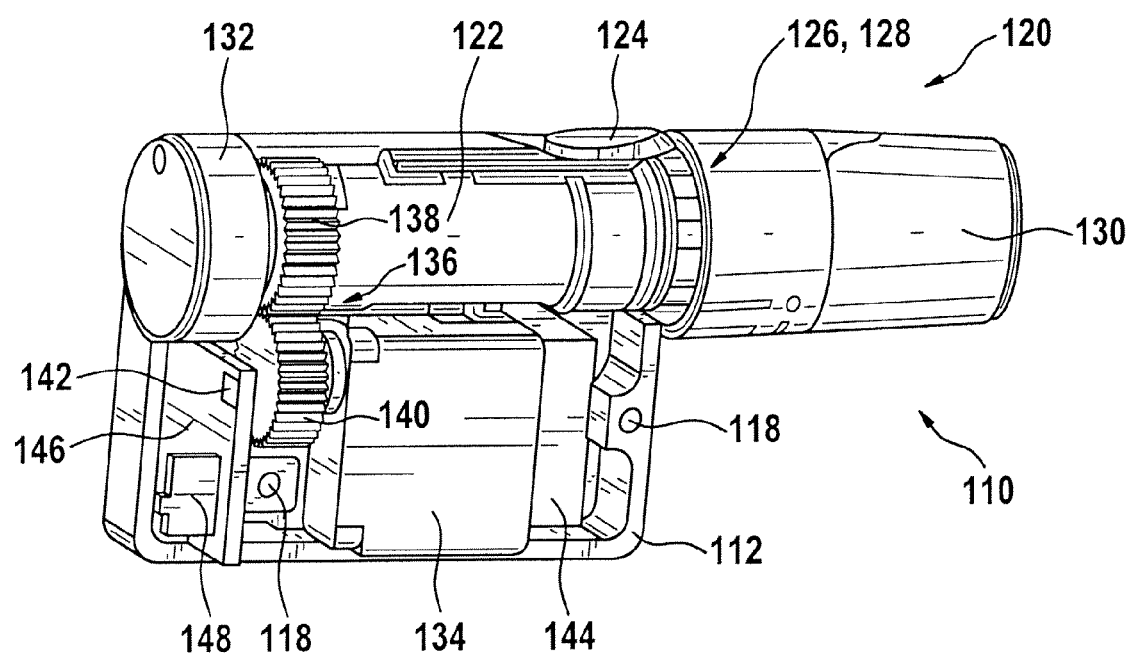
FIG. 1 is a perspective view of a portable lancing aid with a portion of the external housing partially removed.

FIG. 1 shows a perspective view of an embodiment of a portable lancing aid 110. The portable lancing aid 110 has a housing 112 which is shown partially removed in FIG. 1 for the purpose of illustration. A housing cover 114 (see FIG. 2) can be removed from the remaining housing 112 in order to open the housing 112 by loosening screws 116 (see FIG. 2) which connect the housing cover 114 to the remaining housing 112 by appropriate threaded holes 118.

The portable lancing aid 110 additionally has a lancet system 120. The design and mode of operation of this lancet system 120 can, for example, be analogous to the embodiment of the lancet system 120 disclosed in U.S. Pat. No. 7,223,276. Other embodiments of lancet systems can be used such as the lancet system disclosed in U.S. Publication No. 20040260325. The aforementioned U.S. patent and publication are hereby incorporated by reference.

The lancet system 120 has a tensioning device 122 and a release or trigger button 124. In addition, the lancet system 120 has a drum magazine 126 (mostly hidden in FIG. 1) to hold several disposable lancets 128 (not shown). An exemplary drum magazine 126 is described in U.S. Publication No. 20060008389, which is hereby incorporated by reference. The lancet system 120 also has a lancet cap 130 which has an exit hole in the front face (not shown) for the lancet 128 to extend through. The lancet cap 130 is designed to be detached from the lancet system 120 so that the drum magazine 126 can be replaced by removing the lancet cap 130. Furthermore, the lancing depth of the lancets 128 can be adjusted by rotating the lancet cap 130. The drum magazine 126 can be adjusted by means of a rotary knob 132 on the end of the lancet system 120 and thus a new and unused lancet 128 can be selected. In this embodiment, a disposable lancet 128 is selected manually by the user. In an alternative embodiment, a device can be provided in which a new disposable lancet 128 is selected from the drum magazine 126 after each lancing operation.

The portable lancing aid 110 also has a direct current motor 134 in the embodiment shown in FIG. 1. The direct current motor 134 is connected to the tensioning device 122 of the lancet system 120 by means of a drive 136 having two gear wheels 138, 140. Thus, the tensioning device 122 of the lancet system 120 can be tensioned by means of the direct current motor 134. As described above, other electromechanical actuators such as magnetic actuators, piezoactuators or other complex types of motors such as stepping motors can be used.

As shown in FIG. 1, the portable lancing aid 110 has a tensioning status sensor 142 which can detect the tensioning state of the tensioning device 122. In this embodiment, the tensioning status sensor 142 is a sensor which detects the position of the gear wheel 140 and according to this position determines whether the tensioning device 122 is tensioned. This tensioning status sensor 142 can, for example, also be a component of the direct current motor 134 where an angular position of the direct current motor 134 is determined by the position of the gear wheels 138, 140 and/or the drive 136. The tensioning status can be detected if a stepping motor is used instead of a direct current motor 134. However, stepping motors are relatively complicated. Two or more tensioning status sensors 142 can be used instead of an individual status sensor 142 where, for example, a first tensioning status sensor 142 detects the tensioned status of the tensioning device 122 and a second tensioning status sensor 142 detects the untensioned status of the tensioning device 122.

The portable lancing aid 110 shown in FIG. 1 has a rechargeable lithium ion battery 144 and an electronic control circuit board or element 146. The rechargeable lithium ion battery 144 supplies the direct current motor 134 and the electronic control circuit board or element 146 with electrical energy. The high energy density of the rechargeable lithium ion battery 144 typically allows up to about 100 tensioning operations of the tensioning device 122 by the direct current motor 134 with minimal battery size. Furthermore, the discharge of such rechargeable lithium ion batteries 144 is relatively low and thus average use of the portable lancing aid 110 (typically between five and fifteen times per day) requires only periodic recharging of the rechargeable lithium ion battery 144.

The electronic control circuit board or element 146 of the portable lancing aid 110 is designed such that the tensioning status of the tensioning device 122 detected by the tensioning status sensor 142 is used to automatically tension the lancet system 120. As soon as the tensioning status sensor 142 detects that the tensioning device 122 of the lancet system 120 is in an untensioned state (e.g., after triggering the lancet system 120), the direct current motor 134 is started automatically by the electronic control circuit board or element 146 so that the tensioning device 122 is retensioned and the portable lancing aid 110 is thus again ready for operation. Other embodiments of the portable lancing aid 110 are possible in which tensioning the tensioning device 122 by the direct current motor 134 is not triggered until the user makes an affirmative action such as by actuating an appropriate input button on the surface of the portable lancing aid 110.

In the embodiment shown in FIG. 1, the portable lancing aid 110 has an interface 148 which is arranged on the electronic control circuit board or element 146 and protrudes through the housing cover 114 when the housing 112 is closed and can thus be accessed from the outside. This interface 148 can have one or more metal contacts. The rechargeable lithium ion battery 144 can be electrically charged via this interface 148. Furthermore, the portable lancing aid 110 can also be designed such that information can be exchanged via the interface 148, for example, in order to supply the electronic control circuit board or element 146 with information about the patient (e.g., information about the lancing depth of the lancet system 120).

An embodiment of a system for collecting liquid samples 210 is shown in FIG. 2. The system 210 has a portable lancing aid 110 according to the embodiment shown in FIG. 1 (with a closed housing cover 114) and a charging station 212. The portable lancing aid 110 is inserted into an appropriately shaped recess 214 of the charging station 212. This charging station 212 is also shown from above in FIG. 3 where the recess 214 is better illustrated. The charging station 212 has a housing 216 into which the recess 214 forms, and the recess is designed such that the housing 112 of the portable lancing aid 110 can be inserted therein. In this arrangement, the interface 148 of the portable lancing aid 110 is in electrical contact with a charging interface or coupling 310 of the charging station 212 when the portable lancing aid 110 is inserted into the charging station 212. The charging interface or coupling 310 is further connected to a main connection or power cord 218. The charging interface or coupling 310 is advantageously not directly connected to the main connection or power cord 218, but rather via an appropriate electronic circuit that can have switches, an overvoltage protection, a voltage transformer, and/or other electronic components. This ensures that when the portable lancing aid 110 is inserted into the charging station 212, the rechargeable lithium ion battery 144 of the portable lancing aid 110 is electrically charged and is not damaged by incorrect handling or electrical interferences (power fluctuations or short circuits).

The charging station 212 is additionally provided with a flat underside or bottom surface 220 such that the charging station 212 can be safely positioned on flat surfaces without tilting even after the portable lancing aid 110 is inserted. Other exemplary charging stations 212 may have several recesses 214 and charging interfaces or couplings 310 to simultaneously charge several portable lancing aids 110 for use, such as, in hospitals.

FIG. 2 also shows that the portable lancing aid 110 has a charge level indicator 222 on the housing cover 114. This charge level indicator 222 can also be positioned at other sites on the housing 112 and is designed as a segment display having five light-emitting diodes in this embodiment. For example, all five light-emitting diode segments may light up corresponding to the highest charge status of the rechargeable lithium ion battery 144 and none of the segments of the charge level indicator 222 may light up corresponding to the rechargeable lithium ion battery 144 being completely discharged. The light-emitting diode segments can, for example, also have different colors to indicate a low charge status to the user. In particular, the charge level indicator 222 can be actuated by the electronic control circuit board or element 146.

Figure 4:
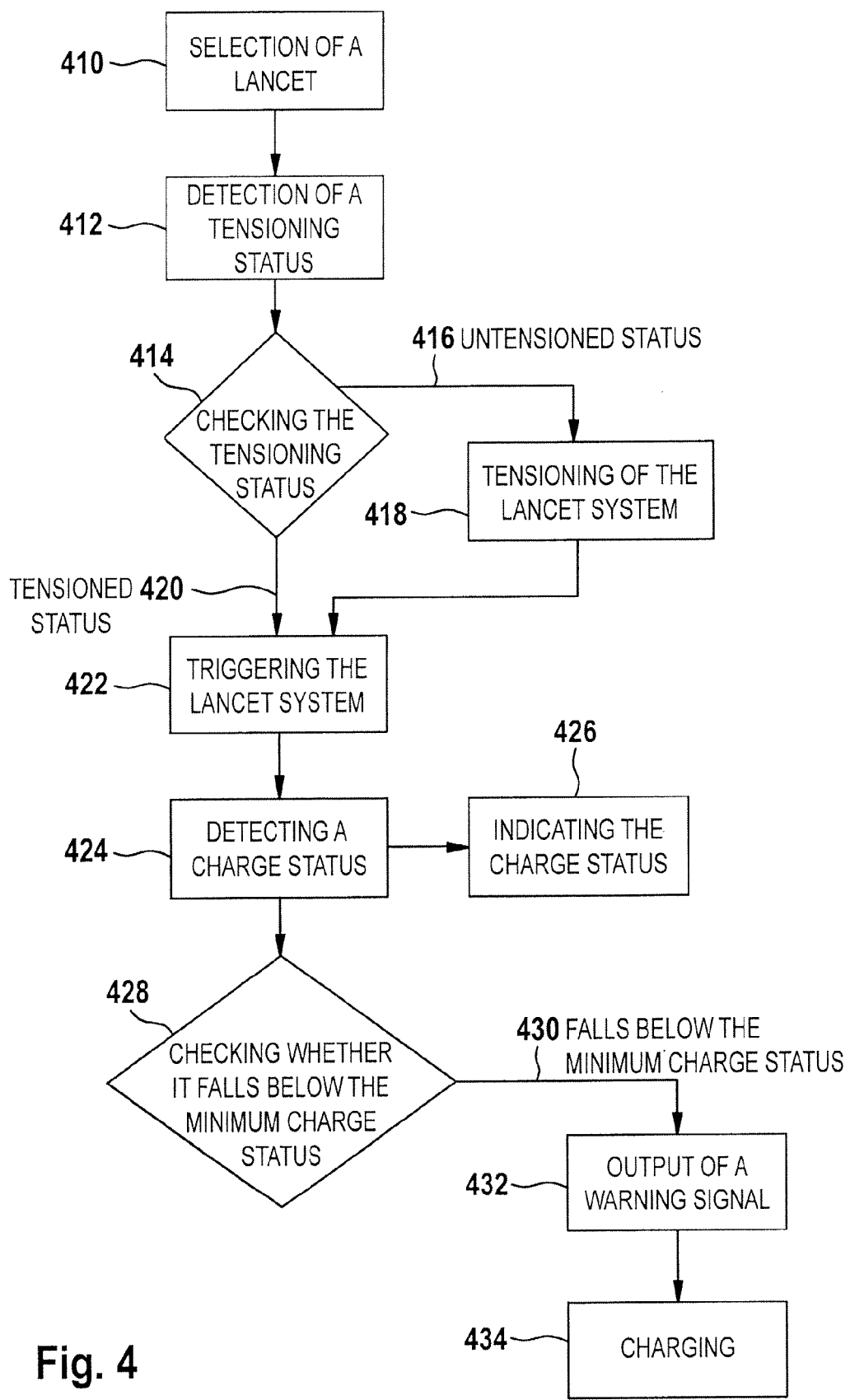
FIG. 4 is a flow chart illustrating a method for collecting blood samples for determining blood glucose concentration.

FIG. 4 shows an exemplary method where the system 210 of FIG. 2 is used to collect liquid samples. The steps shown in FIG. 4 do not necessarily have to be carried out in the order shown and other steps that are not shown can also be performed.

In describing the steps involved in the method of FIG. 4, reference is made to the embodiments shown in FIGS. 1 and 2. In the first step 410, a disposable lancet 128 is selected, for example, by means of the rotary knob 132 of the portable lancing aid 110 of FIG. 1. In the second step 412, the tension of the tensioning device 122 is detected by means of a tensioning status sensor 142. Subsequently, the detected tensioning status is checked in step 414. If it is determined (step 416) that the tensioning device 122 is in an untensioned state, step 418 is carried out and the tensioning device 122 is tensioned by means of the direct current motor 134. If, in contrast, it is determined in step 414 that the tensioning device 122 is already in a tensioned status (step 420), then step 418 (tensioning of the lancet system 120) is skipped. The lancet system 120 is now ready for operation and is triggered in step 422 (for example, by pressing the trigger button 124).

The detection of the tensioning status in step 412 and checking the tensioning status in step 414 can be carried out continuously or periodically so that the lancet system 120 is kept in a tensioned state. Alternatively, as described above, the tensioning 418 of the lancet system 120 can also be initiated by user input.

Finally in step 424, the charge status of the rechargeable lithium ion battery 144 is detected. This detection of the charge status in step 424 does not necessarily take place after the triggering step 422, but rather the detection of the charge status can also, for example, be carried out continuously or at regular intervals or at other stages in the method of FIG. 4. The charge status is indicated to a user of the portable lancing aid 110 in step 426 by means of the charge level indicator 222. A query can also be carried out in step 428 in which the charge status is checked to determine whether the charge status is below a specified minimum charge value. If the charge falls below the minimum charge value (step 430), the user is alerted in step 432, for example, by an acoustic or optical warning signal. Subsequently in step 434, the rechargeable lithium ion battery 144 is recharged by inserting the portable lancing aid 110 into the charging station 212 as shown in FIG. 2, and the charging station 212 is supplied with electrical energy via the main connection or power cord 218.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMERALS 110 portable lancing aid
112 housing
114 housing cover
116 screws
118 threaded holes
120 lancet system
122 tensioning device
124 trigger button
126 drum magazine
128 disposable lancets
130 lancet cap
132 rotary knob
134 direct current motor
136 drive
138 gear wheel
140 gear wheel
142 tensioning status sensor
144 rechargeable lithium ion battery
146 electronic control circuit board or element
148 interface
210 system for collecting liquid samples
212 charging station
214 recess
216 housing of the charging station
218 mains connection or power cord
220 flat underside
222 charge level indicator
310 charging interface or coupling
410 selection of a lancet
412 detection of a tensioning status
414 checking the tensioning status
416 untensioned status
418 tensioning of the lancet system
420 tensioned status
422 triggering the lancet system
424 detecting a charge status
426 indicating the charge status
428 checking whether it falls below the minimum charge status
430 falls below the minimum charge status
432 output of a warning signal
434 charging

What is claimed is:

1. A portable lancing aid for collecting liquid samples, comprising:

a lancet system having a spring system and a lancet wherein the spring system drives the lancet in a puncturing movement;

an actuator that tensions the spring system of the lancet system;

a sensor that detects a tension status of the spring system, wherein the actuator is operable to tension the spring system as a function of the detected tension status;

an energy source connected to the actuator; and an electronic element wherein the sensor transfers the detected tension status to the electronic element, the electronic element triggering the actuator to tension the spring system when the spring system is detected to be in an untensioned state.

2. The portable lancing aid of claim 1, wherein the actuator includes an electric motor.

3. The portable lancing aid of claim 2, wherein the electric motor comprises a direct current motor.

4. The portable lancing aid of claim 1, wherein the lancet system is configured to hold a magazine having a plurality of lancets.

5. The portable lancing aid of claim 1 wherein the energy source is a rechargeable energy source and wherein the lancing aid further comprises an interface configured for connecting the rechargeable energy source to a charging station, the interface being accessible from outside the lancet system.

6. The portable lancing aid of claim 5, further comprising a charge level indicator which displays an electrical charge level of the rechargeable energy source.

7. The portable lancing aid of claim 5, further comprising a charging station to which the portable lancing aid is detachably connectable, the charging station providing electricity to the rechargeable energy source when the portable lancing aid is connected thereto.

8. A system for obtaining liquid samples, comprising:
a charging station;
a portable lancing aid detachably connectable to the charging station, the portable lancing aid comprising:
a lancet system having a spring system and a lancet wherein the spring system drives the lancet in a puncturing movement;
an actuator that tensions the spring system of the lancet system;
a sensor that detects a tension status of the spring system, wherein the actuator is operable to tension the spring system as a function of the detected tension status;
an electronic element wherein the sensor transfers the detected tension status to the electronic element, the electronic element triggering the actuator to tension the spring system when the spring system is detected to be in an untensioned state;
an energy source that supplies power to the actuator; and
an interface configured for connecting the energy source to the charging station, wherein the energy source is recharged by the charging station when the portable lancing aid is connected to the charging station.

9. The system of claim 8, wherein the charging station has at least one coupling adapted to connect to the interface.

10. The system of claim 8, wherein the charging station comprises a recess for receiving the portable lancing aid.

11. The system of claim 8, wherein the charging station comprises a power cord that connects to an external power source.

12. The system of claim 8, wherein the actuator comprises an electric motor.

13. The system of claim 8, wherein the actuator is an electromechanical actuator that tensions the spring system.

14. The system of claim 8, wherein the energy source comprises a rechargeable lithium ion battery.

15. The system of claim 8, wherein the lancet system is configured to hold a magazine having a plurality of lancets.

16. The system of claim 8, wherein the portable lancing aid further comprises a charge level indicator.

17. The system of claim 8, wherein the actuator comprises a magnetic system.

18. The system of claim 8, wherein the actuator comprises a piezoelectric system.

19. The system of claim 8, wherein the actuator comprises at least one gear wheel.

20. The system of claim 8, wherein the actuator is configured to tension the lancet system automatically or manually.

* * * * *